United States Patent [19]
Nigam

[11] Patent Number: 5,978,700
[45] Date of Patent: Nov. 2, 1999

[54] RECOGNIZING VENTRICULAR TACHYCARDIA CONDITION USING DUAL CHAMBER SENSE INFORMATION

[75] Inventor: Indra B. Nigam, Lake Oswego, Oreg.

[73] Assignee: Biotronik Mess-und Therapiegeraete GmbH & Co. Ingenierbuero Berlin, Berlin, Germany

[21] Appl. No.: 09/073,345

[22] Filed: May 6, 1998

Related U.S. Application Data

[60] Provisional application No. 60/045,849, May 7, 1997.
[51] Int. Cl.$^6$ .............................................. A61B 5/0464
[52] U.S. Cl. ........................................................... 600/518
[58] Field of Search .................................... 600/515, 518, 600/519, 521; 607/4, 5, 14

[56] References Cited

U.S. PATENT DOCUMENTS

| | | | |
|---|---|---|---|
| 4,860,749 | 8/1989 | Lehmann | 607/9 |
| 5,002,052 | 3/1991 | Haluska | 607/4 |
| 5,107,850 | 4/1992 | Olive | 600/518 |
| 5,205,283 | 4/1993 | Olson | 600/518 |
| 5,325,856 | 7/1994 | Nitzsche et al. | 607/14 |

*Primary Examiner*—William E. Kamm
*Assistant Examiner*—Kennedy J. Schaetzle
*Attorney, Agent, or Firm*—Venable; George H. Spencer; Robert Kinberg

[57] ABSTRACT

An apparatus for detecting ventricular tachycardia includes a first and second calculation unit, each having an input side connected to a ventricle sensor and an atrium sensor, respectively, and to a timer, for calculating the R—R and P—P intervals between respective successive electrical activities in the atrium and in the ventricle. A threshold value memory stores at least one threshold value for the R—R intervals in memory. A first comparator unit compares the R—R intervals with the at least one threshold value. A first and second interval memory store a predetermined number of calculated R—R and P—P intervals, respectively, or mean R—R and mean P—P interval values. A second comparator unit compares the P—P intervals with the R—R intervals. A third and fourth calculation unit, connected to the output of the first and second calculation unit and/or of the first and second interval memory unit, respectively, calculate the change over time between successive P—P and R—R intervals. First and second criterion memories stores predetermined stability criterion for the change over time between successive P—P and R—R intervals, respectively. A third and fourth comparator unit compare the calculated change over time in the P—P and R—R intervals with the associated stability criterion stored in memory.

10 Claims, 10 Drawing Sheets

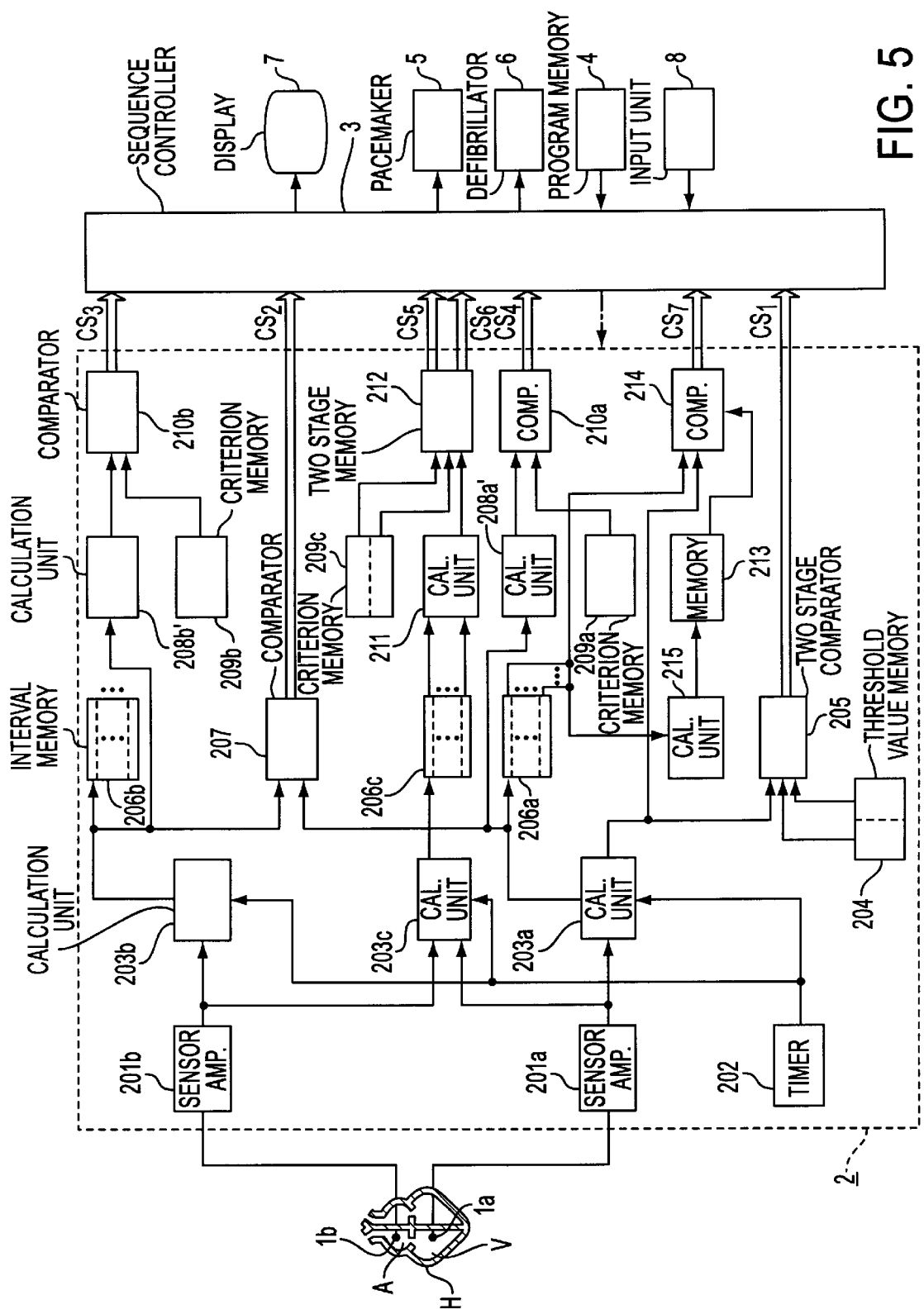

RECOGNIZING VENTRICULAR TACHYCARDIA CONDITION USING DUAL CHAMBER SENSE INFORMATION

CROSS REFERENCE TO RELATED APPLICATION

This application claims the benefit of Provision Application No. 60/045,849 filed May 7, 1997, the benefit of which is claimed and the subject matter of which is incorporated herein by reference.

BACKGROUND OF THE INVENTION

The invention relates to an apparatus for detecting ventricular tachycardia. Such an apparatus can be made in the form of an independent diagnostic unit or as a component of a cardiac pacemaker with an antitachycardia operating mode or in the form of a defibrillator or cardioverter.

The treatment of tachycardial disturbances in heart rhythm is one of the most important tasks in cardiology and in particular is a primary field for the use of electrical stimulation of the heart. In view of the manifold forms such problems can take and their manifold causes, extensive attempts have been made for years to improve the preconditions for therapeutic success by refining the classification of tachycardial arrhythmias and associating them more exactly with typical defects in the cardiac stimulus conduction system.

Because pathological ventricular tachycardias (hereinafter also abbreviated "VT") are so widespread and so needful of treatment on the one hand, and because they have a good chance of successful treatment with special pacemaker pulse trains on the other, reliably distinguishing them from other arrhythmias, and especially physiological tachycardias, ventricular fibrillations ("VF") or supraventricular tachycardia ("SVT")—including under special circumstances—has proven to be an especially important problem.

In German Patent Application DE-A 44 39 256, it is proposed that the relative distribution of heartbeat intervals, which can be considered as fibrillation intervals or tachycardia intervals, within predetermined time ranges can be utilized to classify the prevailing type of arrhythmia. This is intended to take proper account of the fact that in practice, the interval lengths in ventricular tachycardia on the one hand and fibrillation on the other often overlap considerably.

A great many other approaches—which will not be described in detail here—to solving these problems seek to employ analysis of the three-dimensional propagation or correlation of depolarizations in the cardiac tissue. This requires implanting many electrodes for signal detection—sometimes even pericardially—and for this reason, if for no other, has little chance of being realized.

In U.S. Pat. No. 4,860,749, a method for distinguishing ventricular tachycardia from a sinus or other kind of supraventricular tachycardia is described, in which the atrial heart rate and the ventricular heart rate (the inverse values of each will hereinafter also be called the "P—P interval" or "R—R interval") as well as the A-V interval (hereinafter sometimes also called the "P-R interval") are measured. If the R—R interval is within a predetermined range and is shorter than the P—P interval, then the condition is readily classified as ventricular tachycardia. If the atrial and the ventricular rate are approximately the same as a consequence of 1:1 A-V conduction or retrograde conduction, then the measured A-V interval is subjected to a comparison with a predetermined value ("sinus A-V interval"), and the classification criterion is obtained from the outcome of the comparison.

In U.S. Pat. No. 5,325,856, a method for distinguishing between ventricular and supraventricular tachycardias is proposed, which is based on a comparison of the divergence over time in the P-R and R—R values with two predetermined threshold values at the onset of the tachycardia.

U.S. Pat. No. 5,327,900 describes a method for distinguishing between pathological and physiological (sinus) tachycardias at a comparable atrial and ventricular rate, which is based on the association of the measured A-V interval with a predetermined A-V time slot, which has been determined from the A-V interval during normal sinus rhythm. This algorithm is comparatively simple; however, thus far there is no proof of its being efficient enough to make such distinctions.

European Patent Application EP-A 0 597 459 describes a method in which if the R—R and P—P intervals agree, a comparison is first made between the length of the A-V (P-R) interval and a predetermined base value, and finally—if that comparison does not produce a conclusive result—a test stimulation in the atrium is performed, and the classification is made on the basis of the stimulated heart response, in particular changes over time in the R—R intervals.

SUMMARY OF THE INVENTION

The object of the invention is to provide an apparatus which makes reliable recognition of ventricular tachycardia—requiring proper therapeutic intervention—possible at reasonable technological effort and expense and with little stress on the patient. In particular, the apparatus should enable improved recognition of ventricular tachycardia when atrial tachyarrhythmia is simultaneously present.

The above and other objects are achieved according to the invention by the provision of an apparatus for detecting ventricular tachycardia, comprising an atrium sensor for sensing electrical activity in an atrium and a ventricular sensor for sensing electrical activity in a ventricle of heart;

a timer for detecting the instant of occurrence of the respective electrical activity;

a first and second calculation unit, each having an input side connected to the ventricle sensor and the atrium sensor, respectively, and to the timer, for calculating R—R or P—P intervals between successive electrical activities in the ventricle and in the atrium, respectively, and for selectively forming mean R—R and mean P—P interval values over a predetermined period of time or a predetermined number of calculated R—R and P—P intervals, respectively;

a threshold memory for storing at least one threshold value for the R—R intervals or mean R—R interval values;

a first comparator unit, connected to the outputs of the first calculation unit and the threshold value memory, for comparing the R—R intervals or mean R—R interval values with the at least one threshold value and for outputting a first classification signal characterizing the outcome of the comparison;

first and second interval memory units, connected to the output of the first and second calculation units, respectively, for storing a predetermined number of respective calculated R—R or P—P intervals, or mean R—R or mean P—P interval values in memory;

a second comparator unit, connected to the output of one of (a) the first and second calculation units and (b) the first and second memory units, for comparing the P—P intervals with the R—R intervals for outputting a second classification signal characterizing the outcome of the comparison;

a third and fourth calculation unit, connected to the output of at least one of (a) the first and second calculation units and (b) the first and second interval memory units, respectively, for calculating a change over time between successive R—R and P—P intervals or the mean R—R and mean P—P interval values;

first and second criterion memories for storing, respectively, a predetermined stability criterion for the changeover time between successive R—R and P—P intervals or mean R—R and mean P—P interval values; and a third and fourth comparator unit, each having an input side connected to the output of the third and fourth calculation units, respectively, and to the first and second criterion memories, respectively, for comparing the calculated change over time in the R—R or P—P intervals with an associated stability criterion stored in the respective criterion memory and for outputting a third and fourth classification signal characterizing the outcome of the comparison.

The invention thus provides for an apparatus which includes means for performing a multistage classification process, based solely on the signals of spontaneous heart activity picked up with one sensor each in the atrium and the ventricle, in which process the length of the R—R, P—P, and if needed the P-R intervals are also evaluated, fundamentally on a beat-to-beat basis, both quantitatively and in terms of their development over time (with regard to their stability, regularity, or the monotony of a change over time).

Since this does not require determining and analyzing either the EKG curve form or the three-dimensional propagation of the depolarizations in the cardiac tissue, this apparatus is comparatively uncomplicated to produce and implant. Further, during both implantation and while it is in operation, it puts no greater stress on the patient than a conventional pacemaker/cardioverter.

For every R—R interval that has elapsed, it is first ascertained, by means of a threshold value discrimination, whether its length justifies its being classified within the rate range of ventricular tachycardia ("VT zone"). If so, then a number of further criteria are employed. These are in particular the following criteria:

a) sudden onset, b) interval stability and P-R interval regularity, c) monotony of the change over time in the P-R intervals, d) ratio between R—R and P—P interval length.

In the normal case, several, but not necessarily all, of these criteria, need to be tested. Sometimes, the checking is expediently done using mean interval values, which have been formed taking at least three previous intervals into account. How these criteria are defined and tested will be explained later herein.

VT is accordingly present if (given an R—R interval length that is within the VT zone) the mean value of the R—R interval length is less than that of the P—P interval length.

Conversely, if the P—P interval length is less than the R—R interval length, then the stability of the R—R intervals must be tested as well, and the ratio of the R—R and P—P interval lengths must be formed. If stability is found, and if the R—R interval length is not a multiple of the P—P interval length, then once again VT is occurring.

If the R—R and P—P interval lengths are approximately equal, then the P-R intervals must be evaluated in addition. VT is occurring if the R—R intervals are not stable and the P-R intervals are not regular, or the R—R intervals are stable but the P—P intervals are not, or both the R—R and the P—P intervals are stable, and the P-R intervals are varying monotonously, or both the R—R and the P—P intervals are stable and a sudden onset has occurred.

BRIEF DESCRIPTION OF THE DRAWINGS

Advantageous further features of the invention will be described in further detail below along with the description of the preferred embodiment of the invention in conjunction with the drawings. Shown are:

FIG. 5, a function block diagram of another embodiment of the apparatus according to the invention.

DETAILED DESCRIPTION OF THE INVENTION

Figure 1:
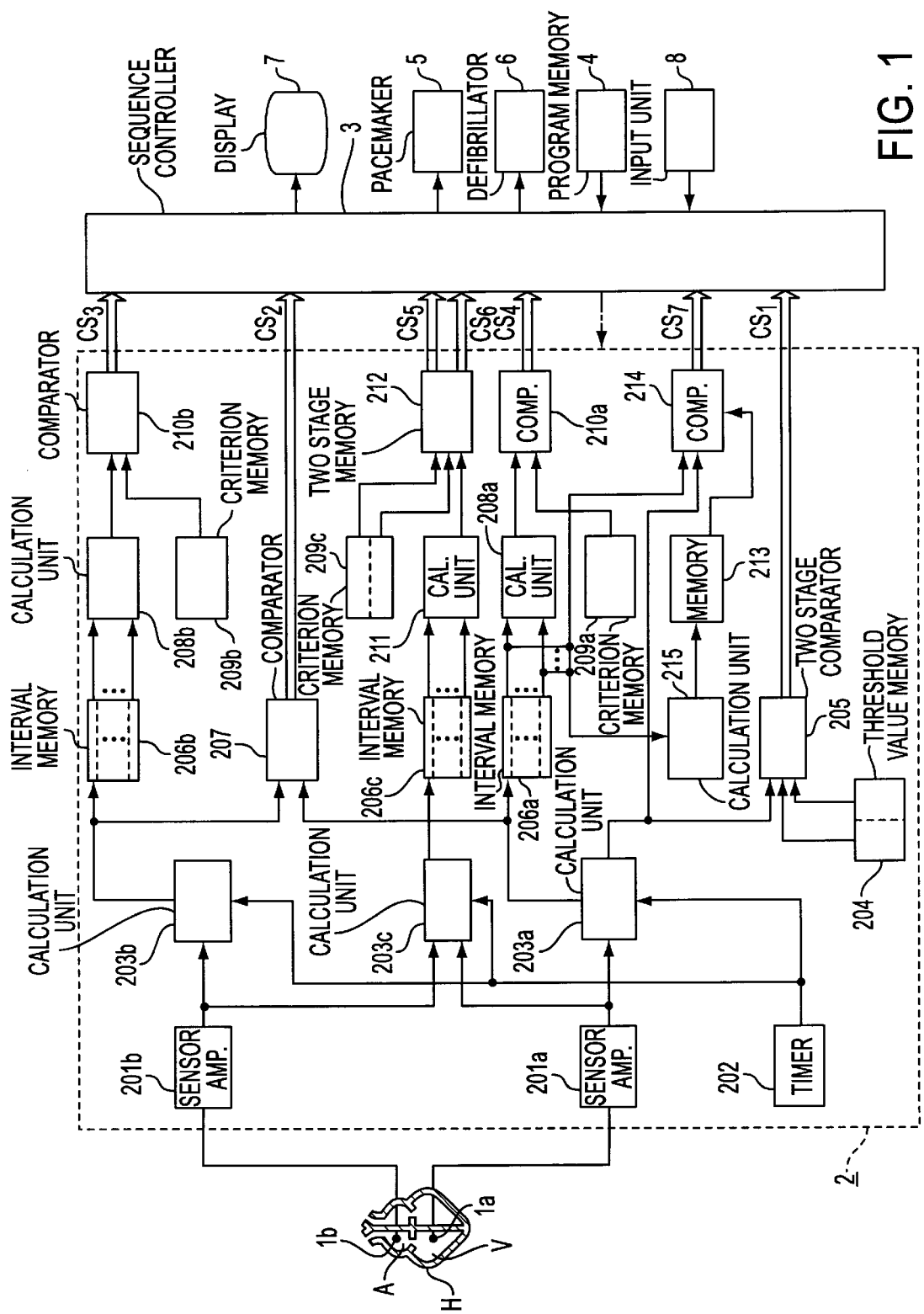
FIG. 1, a function block circuit diagram of an apparatus according to an embodiment of the invention.

In FIG. 1, the layout of an apparatus 2 for classifying tachycardia, especially for detecting ventricular tachycardia, and connected to a heart H via a ventricle electrode 1a and an atrium electrode 1b acting as endocardial signal pickups, is shown in an embodiment of the invention in terms of its essential function elements. The apparatus 2 is controlled via a sequence controller 3 in accordance with a sequence to be explained hereinafter that is stored in memory in a program memory 4. On the basis of classification data ascertained by the apparatus, a pacemaker 5 or defibrillator 6—which are known per se—is selectively triggered for initiating a suitable electrotherapy. The classification data that are output by the apparatus 2 may be shown on an optional display unit 7 (symbolized by dotted lines) and thus if necessary may also be utilized independently of the initiation of electrotherapy—for instance to determine therapy using medication. An input unit 8 for entering patient-specific data pertaining to the execution of a specific classification procedure is optionally provided as well.

The apparatus 2 is preferably embodied, together with the controller 3, as an implantable apparatus and as an integral component of an automatic pacemaker/defibrillator, and in that case is connected via known telemetry devices (not shown) to the display unit 7 and input unit 8, which are especially contained in an external programming device. This allows constant, virtually real-time monitoring of the cardiac activities of a patient for the occurrence of tachycardial rhythm disturbances and their type, and for the immediate initiation of proper electrotherapy.

However, for special applications—such as for use during heart surgery—at least some parts of the apparatus 2 and/or of the controller 3 may be embodied in an external device instead.

In both cases, the practical embodiment will advantageously be done using a microprocessor structure or may be executed partly on an ASIC (customized) basis; the function elements described below are realized at least in part by software.

As shown in FIG. 1, the apparatus 2 has a sensor amplifier 201b, connected to the atrial sensor electrode 1b, for sensing electrical activity (the P waves) in the atrium A of the heart H, and a sensor amplifier 201a connected to the ventricular sensor electrode 1a for sensing electrical activity (especially the R waves or QRS complexes) in the ventricle V of the heart H. A timer or clock 202 is also provided for detecting the instant of occurrence of the particular electrical activity.

A first calculation unit 203a, connected on the input side to both the ventricle electrode 1a and the timer 202, ascertains the (averaged) time intervals between successive electrical activities in the ventricle (R—R intervals). In the simplest embodiment, it is basically an R-wave-triggered counter for the pulses of the timer, but in the preferred embodiment it executes averaging of the counted values over a number of R waves.

Analogously, a second calculation unit (or in the simplest version a P-wave-triggered counter) 203b connected on the input side to the atrium electrode 1b and to the timer 202 serves to ascertain the P—P intervals and average them over time. The averaging of the measured time intervals in the first and second calculation units 203a, 203b is done in a manner known per se by means of an integration or averaging device (not shown); by way of example, a number of four detected heart actions is made the basis of the calculation (see FIG. 1b).

A dual-range threshold value memory 204 is used to store a lower and an upper threshold value for the R—R intervals (or mean R—R intervals), of which the upper threshold value defines a range of normal cardiac activity as opposed to a range of tachycardial rhythm disturbances, and the lower threshold value defines a range toward the top of heart activity that can be classified unequivocally as ventricular fibrillation. Connected to the outputs of the first calculation unit 203a and of the threshold value memory 204 is a two-stage comparator 205, for comparing the ventricle time intervals (or mean ventricle time intervals) with the upper and lower threshold values and for outputting a first classification signal $cs_1$ that characterizes the outcome of the comparison—that is, the location of the R—R intervals ascertained within one of the aforementioned ranges.

Connected to the outputs of the first and second calculation units 203a, 203b are a first and second interval memory 206a, 206b, for storing a predetermined number of calculated ventricular or atrial time intervals or mean time interval values, as well as a further comparator stage 207 for comparing the atrial time intervals with the ventricular time intervals and for outputting a second classification signal $cs_2$ that characterizes the outcome of the comparison. The interval memories 206a, 206b are serial memories and in particular are organized on the LIFO principle. The layout of the comparator stage 207 is shown in more detail in FIG. 1a and will be described hereinafter.

A third calculation unit 208a is also connected to the output of the first interval memory 206a, and a fourth calculation unit 208b is also connected to the output of the second interval memory 206b. The third and fourth calculation units execute a calculation of the change over times between successive R—R or P—P intervals (or mean R—R and mean P—P interval values), stored in the interval memories beforehand, and at their output furnish the corresponding differential or quotient values.

A first and second criterion memory 209a, 209b serve to store a respective predetermined stability criterion for the change over time between successive R—R and P—P intervals. A comparator stage 210a, 210b connected on the input side to the output of the third and fourth calculation unit 208a, 208b, respectively, and the associated respective criterion memory 209a, 209b, serves to compare the calculated change over time in the P—P and R—R intervals, respectively, with the associated stability criterion stored in memory and to output a third and fourth classification signal $cs_3$ and $cs_4$, respectively, characterizing the outcome of the comparison.

A fifth calculation unit 203c, which in the simplest version is embodied as a counter triggered by successive P and R waves, is connected on its input side to both the atrium electrode 1b and the ventricle electrode 1a and also to the timer 202, and it determines the P-R intervals optionally—averaged over time—which are often also called A-V intervals. Connected to the output of the fifth calculation unit 203c is a third interval memory 206c for the P-R or A-V intervals (or mean values of them). Connected to the output of this memory 206c is a sixth calculation unit 211, for calculating the change over time in the P-R intervals and for outputting a differential value or quotient as a measure of the change over time.

A third criterion memory 209c, organized as a multirange memory, stores on the one hand a predetermined regularity criterion and on the other a predetermined monotony criterion for the change over time between successive P-R intervals (naturally, separate memories may also be used for this purpose). A two-stage comparator and calculation unit 212 connected on the input side to the output of the fifth calculation unit 211 and to the third criterion memory 209c executes a comparison of the calculated change over time in the P-R intervals with the regularity criterion stored in memory, or—if the comparison in the first stage shows that this criterion is not met—with the monotony criterion also stored in 209c, and outputs a fifth and sixth classification signal $cs_5$ and $cs_6$, respectively, characterizing the outcome of comparison, which expresses the regularity and monotony, respectively, of the behavior over time of the P-R interval.

A further memory 213 is provided for storing a ventricular comparison interval.

A further comparator unit 214 is connected on the input side to the outputs of the first calculation unit 203a on the one hand and of the first interval memory 206a and on the other, and—via an additional input—to the comparison value memory 213; the comparator unit executes a comparison of the current ventricular time interval (or mean ventricular time interval value) with a ventricular comparison interval stored in memory and thereupon outputs a seventh classification signal $cs_7$. The comparison value memory 213, in the version shown, is connected on the input side with a comparison value calculation unit 215, which in turn is connected on the input side to the output of the first memory unit 206a and on an ongoing basis, on the basis of the most recent R—R intervals determined in the past (stored in the memory 206a) calculates the differential ventricular amount that is definitive for the comparison in the comparator 214.

Figure 1A:
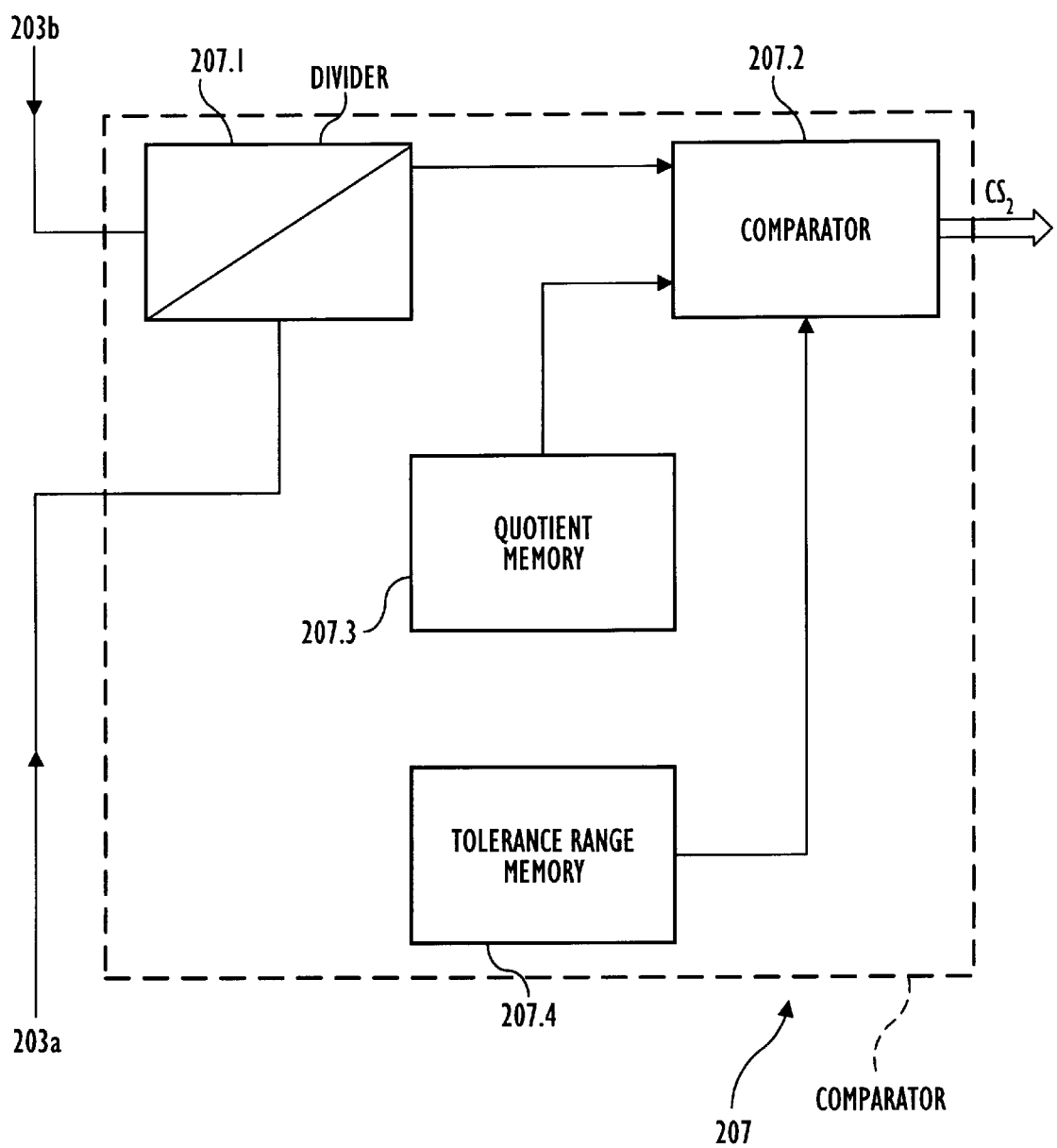
FIGS. 1a and 1b, function block diagrams of the internal layout of function units of the apparatus of FIG. 1.

FIG. 1a shows the internal layout of the comparator stage 207: The two inputs of a divider stage 207.1 are connected to the outputs of the calculation units 203a and 203b (not shown in this drawing figure), and this stage executes a division of the respectively supplied R—R interval by the associated P—P interval, and its output is connected to one input of a comparator stage 207.2, to which it supplies the calculated current value of this quotient. The other comparison signal input of the comparator stage 207.2 is connected to a quotient memory 207.3, in which fixedly predetermined (integral) values for the R—R/P—P quotient are stored in memory, and which can therefore be embodied as a read-only memory (ROM). In a further memory 207.4, preferably embodied as a reprogrammable memory (such as a EEPROM), a quotient tolerance value is stored, which is furnished via a third input to the comparator stage 207.2. The second classification signal $cs_2$ output at its output thus—within the limits of the predetermined tolerance range—expresses whether the R—R interval/P—P interval quotient is integral.

Figure 1B:
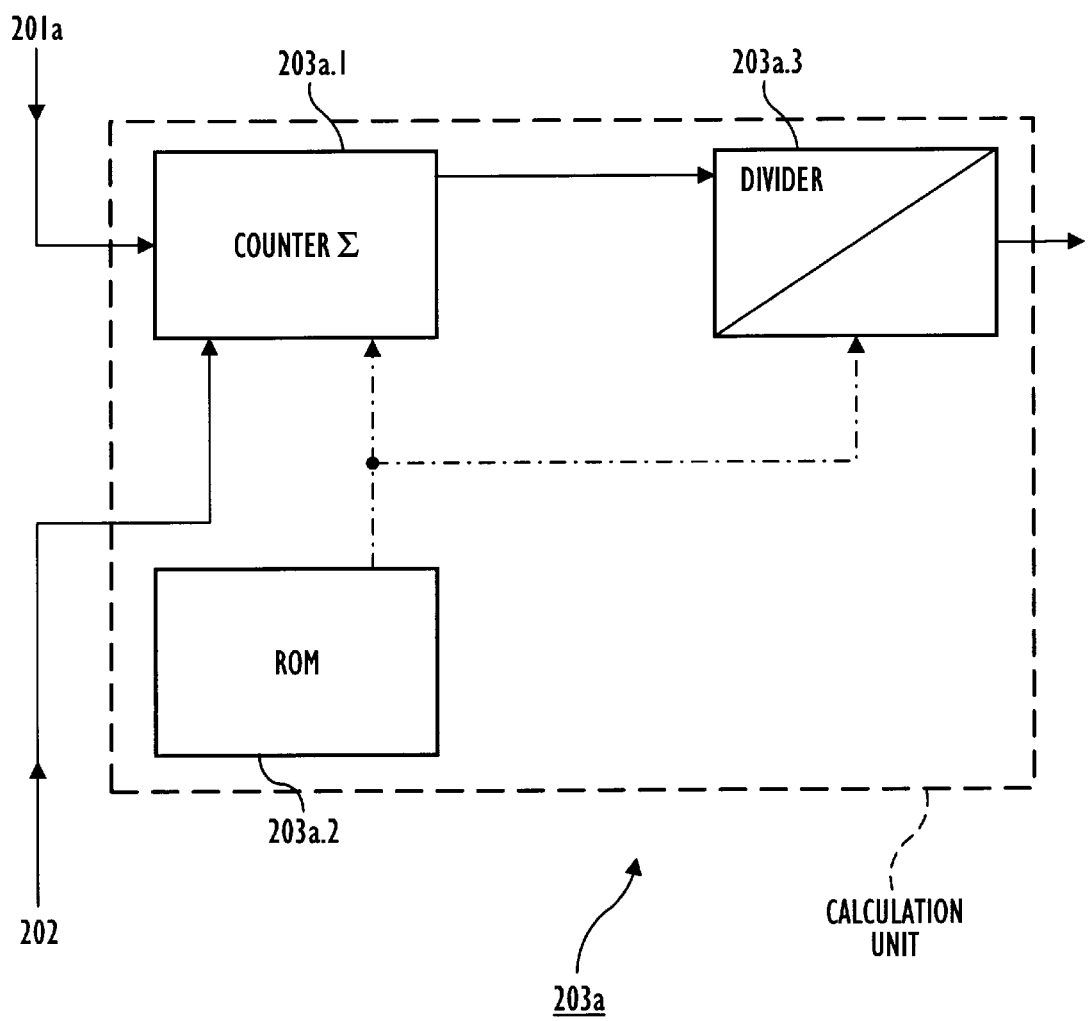

FIG. 1b is a schematic illustration of the layout of the calculation units 203a and 203b in the version with averaging over time of the measured interval values, shown with the unit 203a as an example. The heart action signal delivered by the ventricle reading amplifier 201a and the time or clock signal of the timer 202, as well as an interval number value n (for instance, n=4) stored in a ROM 203a.2 control a counter 203a.1; the timer signals are delivered to the counting input and are counted until the $n^{th}$ detected R wave is processed as a reset signal, whereupon the counter 203a.1 determines the total duration of n R—R intervals and outputs it to an input of a divider stage 203a.3. The other input of this stage is connected to the output of the interval counting memory 203a.2, in such a way that it performs a division of the total duration by the number of intervals and thus furnishes the R—R interval averaged over n intervals. The calculation unit 203b is embodied analogously in layout and function but is connected to the atrium reading amplifier 201b and determines the mean P—P interval duration.

In a third calculation unit 203c, the determination of the P-R intervals averaged over time is done in a corresponding way; here, the detected P and R waves form separate starting and stopping reset signals of an interval length counter.

The operation of the apparatus, described above in terms of its fundamental layout, will be described below in conjunction with FIGS. 2a–2c, which together show a flowchart of the procedure for detecting ventricular tachycardia or distinguishing it from a sinus or other supraventricular tachyarrhythmia. This procedure is especially advantageous in the simultaneous presence of an atrial tachyarrhythmia, which proceeds at the same or a higher rate as the tachyarrhythmia that has been detected in the ventricle and is to be classified.

After the procedure starts, in the first calculation unit 203a the time interval between two successive R wave signals (the R—R interval), sensed in a manner known per se by the ventricle electrode 1a and processed in the associated reading amplifier 201a, is determined.

In two successive steps S1 and S2, via the comparator 205, first in a comparison with the interval threshold values stored in the memory 204 an association is made with one of the interval or rate ranges, that is, (1) "normal" sinus activity (relatively long interval values or relatively low rate values), or (2) tachyarrhythmia conditions to be classified in further detail (medium-sized interval or rate values for a tachyarrhythmia condition), or (3) a fibrillation range (very short interval values or high rate values). The two threshold values are patient-specific and should be programmed by a physician.

If it is found that the interval value is located neither in a tachycardial range (2) ("no" in step S1) nor in the fibrillation range (3) ("no" in step S2) and thus is in the range (1), then there is no need to initiate electrotherapy ("stop" after S2). Conversely, if it is within range (3) ("yes" in step S2), then as a rule via the controller (3), which has received and processed the corresponding classification signal $cs_1$, the defibrillator (6) is triggered and defibrillation or cardioversion is initiated. Optionally, the physician can also administer medication quickly, as soon as the outcome of classification shown on the display 7 tells him ventricular fibrillation is occurring.

If the current R—R interval or ventricular rate value is located in range (2) or (3) ("yes" in step S1), then in a step S3 it is additionally asked whether the tachyarrhythmia was of sudden onset. To that end, the currently ascertained mean R—R interval value available at the output of the first calculation unit 203a is subjected in the comparator 214 to a comparison with the preceding mean value or values, which can be called up from the first interval memory 206a. (The function elements additionally required for forming the mean values are familiar to one skilled in the art and for the sake of greater simplicity are not shown in FIG. 1.) The classification signal $cs_7$ output by the comparator 214 expresses whether a shortening of the R—R interval exceeding the allowable differential amount stored in the comparison value memory 213 is present, which can be evaluated as proof of a sudden onset of the tachyarrhythmia.

The classification signal $cs_7$ that confirms a sudden onset is stored (in a storage region of the controller 3 not shown in FIG. 1), until a predetermined number (for instance 4) of heart activities has occurred within range (1). It is used as a classification criterion in a condition described hereinafter.

Figure 2A:
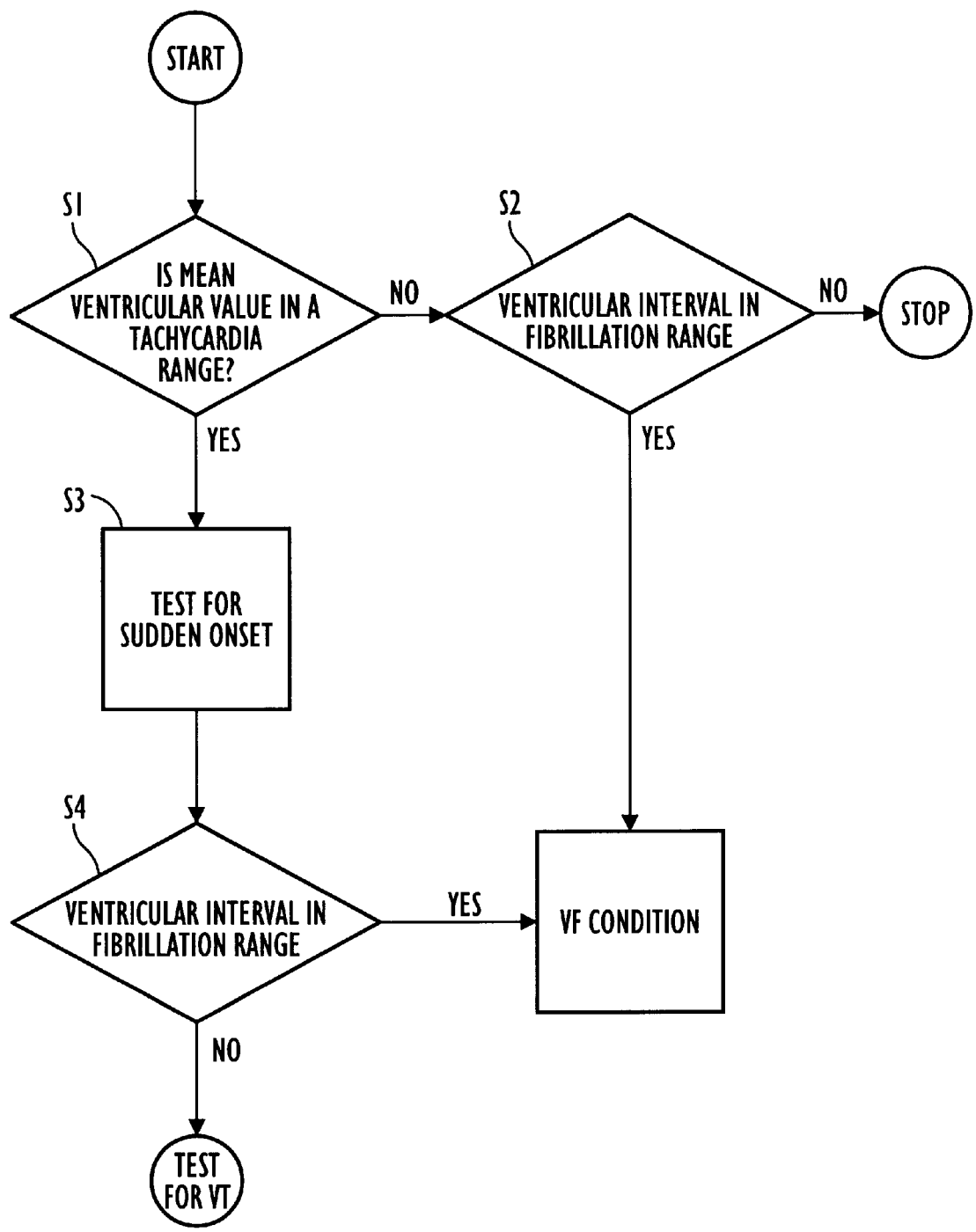
FIGS. 2a–2c, a flowchart of the procedure for detecting ventricular tachycardia by means of an apparatus of FIG. 1.
Figure 2B:
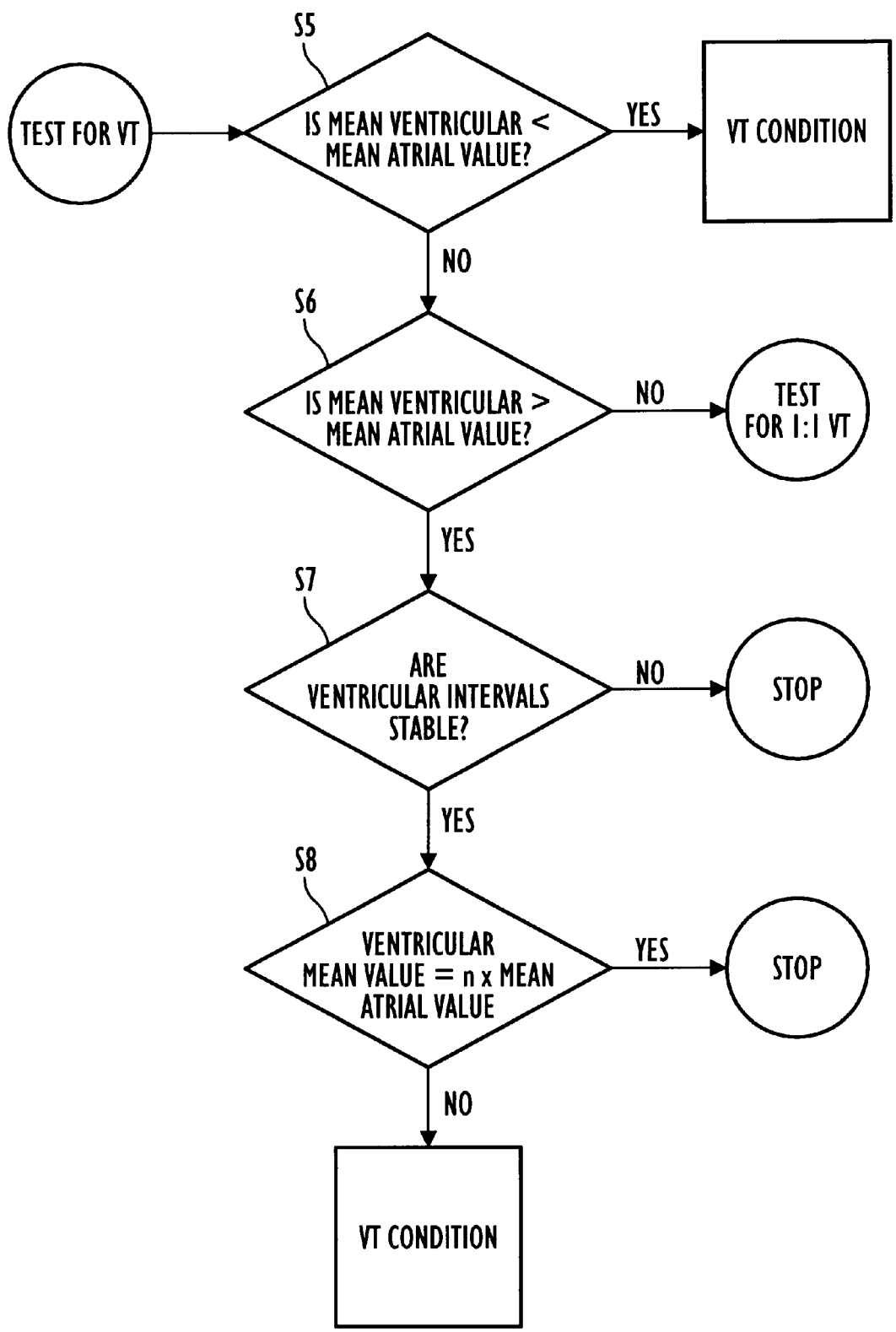

Step S4 in FIG. 2a asks, after the question of sudden onset, again whether the R—R interval value is within the aforementioned range (3). If so ("yes" in step S4), then ventricular fibrillation ("VF condition") is occurring, which must be treated as above in the case of "no" in step S2. If not ("no" in step S4), then for classifying the tachyarrhythmia further criteria are tested ("Test for VT"—see below in conjunction with FIG. 2b). In a step S5, in the comparator stage 207, a comparison is made between the R—R intervals (mean values) and the P—P intervals (mean values) that are furnished at the output of the second calculation unit 203b. If the R—R intervals are shorter than the P—P intervals ("yes" in step S5), then ventricular tachycardia ("VT condition") is occurring. If the mean R—R interval values are not shorter than the mean P—P interval values ("no" in step S5), then the process continues in the flow chart in a step S6, in which the question is asked whether they are longer than the mean P—P interval values. In practice this step can be performed in the same operation as S5. If this is not the case ("no" in step S6), then the process continues with a "Test for 1:1 VT"—see hereinafter and FIG. 2c. Conversely, if so ("yes" in step S6), then the process continues in step S7.

In step S7, the question is asked whether the R—R intervals are stable over time. To that end, the outcome of calculation by the third calculation unit 208a is subjected in the comparator 210a to a comparison with a stability criterion programmed (in milliseconds or percent) and stored in the criterion memory 209a. In practice, the differences between the current one and each of the three preceding mean R—R interval values are preferably compared with the stability criterion, and stability is assumed to exist if the criterion is met in all three comparisons. If the R—R or ventricular intervals are not stable ("no" in step S7), then the test is discontinued ("stop") upon the finding that no VT is present.

Conversely, if they are stable ("yes" in step S7), then the process continues in a step S8. In step S8, the question is asked in the comparator stage 207 whether the mean R—R interval value picked up from the output of the first calculation unit 203a is an integral multiple of the mean P—P interval value picked up from the output of the second calculation unit 203b. This process has been described above in conjunction with FIG. 1a. If it is found that the mean R—R value is an integral multiple of the mean P—P value ("yes" in step S8), then the test is discontinued ("stop")—again with the finding that no VT is occurring. In that case, what is occurring is an atrial tachycardia conducted at n:1 into the ventricle. Conversely, if it is found that it is not an integral multiple ("no" i step S8), then VT is occurring.

Figure 2C:
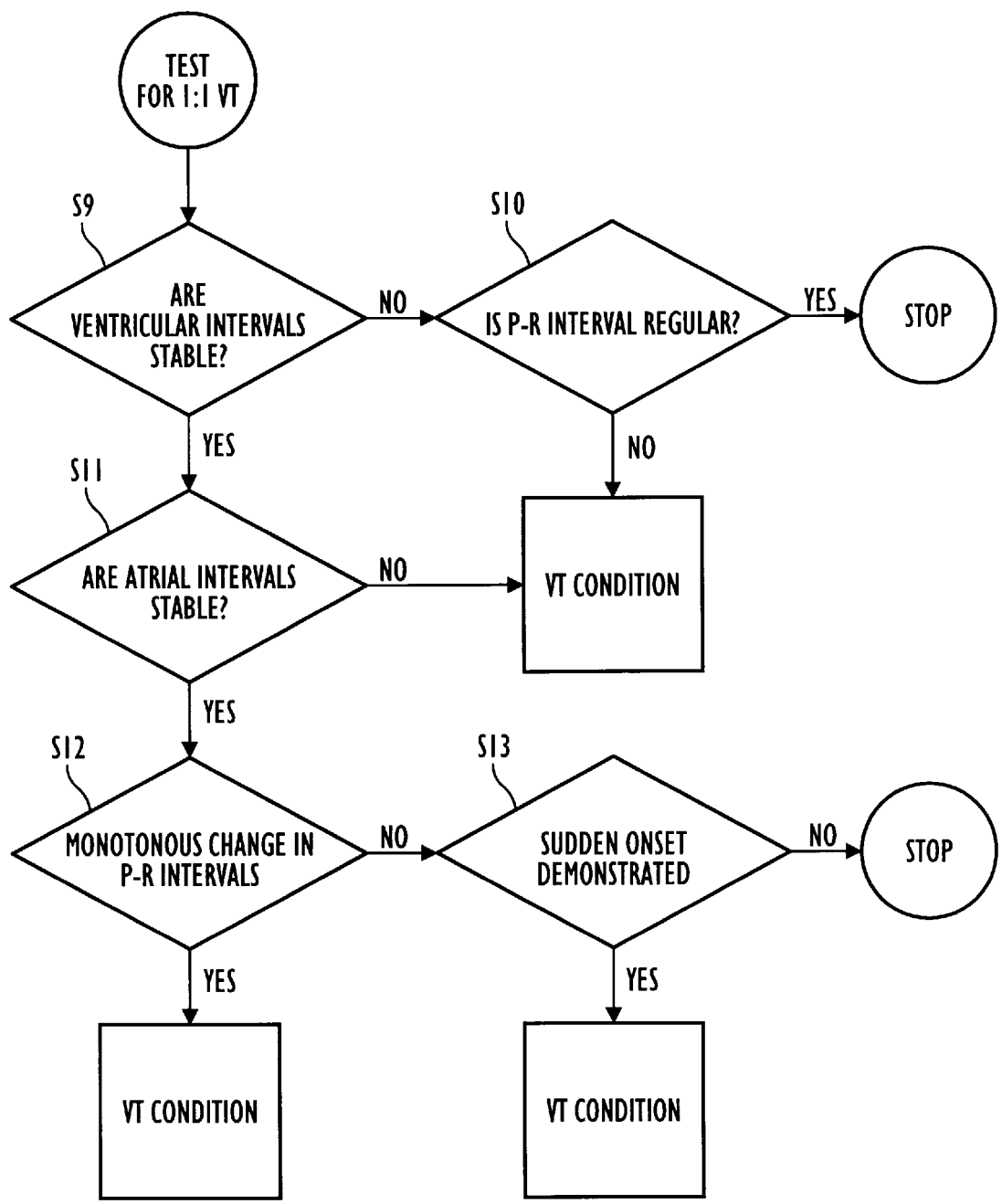

Step S9, which is the first step in the test, shown in FIG. 2c, for the presence of a 1:1 ventricular tachycardia, corresponds to the above step S7. If it is finally found that the ventricular intervals are not stable ("no" in step 5), then in a step S10 it is asked whether the P-R intervals are regular. To that end, the outcome of calculation by the fifth calculation unit 211 is subjected in the comparator and calculation unit 212 to a comparison with a program regularity criterion stored in the memory 209c. To that end, in the practical version, preferably half of the value of the aforementioned stability criterion is set for the R—R intervals, and the comparison is performed for a plurality of previous P-R interval values. If it is found here that the regularity condition is met ("yes" in step S10), then it is certain that VT is not occurring, and the test is discontinued. Conversely, if this condition is not met, then ventricular tachycardia is occurring ("VT condition").

Conversely, if it is ascertained in step S9 that there is stability with regard to the R—R intervals, then the process continues in a step S11, in which in the same way, by means of the fourth calculation unit 208b with recourse to the P—P intervals stored in the second interval memory 206b, the stability of the atrial or P—P intervals is tested. If these intervals prove not to be stable, then once again a VT condition exists. If conversely they are stable, the process continues in a step S12.

In step S12, the question is asked whether the change over time in the P-R intervals is monotonous. To that end, the outcome of calculation by the fifth calculation unit 211 is subjected in the comparator and calculation unit 212 to a comparison with a programmed monotony criterion stored in the memory 209c. Once again, this comparison includes an evaluation of the development over time for the last four mean P-R intervals, and the monotony criterion comprises the fact that in the order over time of all four intervals, each subsequent interval is either longer or shorter than the proceeding one:

$$P\text{-}R(t1) \leq P\text{-}R(t2) \leq P\text{-}R(t3) < P\text{-}R(t4), \text{ where } t1 \leq t2 < t3 < t4,$$

or $$P\text{-}R(t1) \geq P\text{-}R(t2) \geq P\text{-}R(t3) \geq P\text{-}R(t4), \text{ where } t1 < t2 < t3 < t4.$$

If in this sense monotony exists ("yes" in step S12 then the condition should be classified as ventricular tachycardia.

If there is no monotony ("no" in Step S12), then the process continues in a final step S13. In step S13, recourse is had to the stored statement on the presence or absence of a sudden onset of the tachyarrhythmia (see the description above for S3). If there is no such sudden onset, then—under the other preconditions of the steps performed up to now—no VT is occurring, either. Conversely, if a sudden onset has been found, then the arrhythmia—if the other criteria are met—is a VT.

The definitive statement regarding the presence of a ventricular tachycardia is made if performing the above procedure multiple times (at various instants within a testing time period, with whatever interval values are then valid) has shown that the criteria for the "VT condition" are met without any "normal" ventricular condition ("stop" in FIG. 2a) having been found in the mean time. If a "normal" condition is found, then the counting value of "VT condition" is set to zero, and the procedure is begun again from the beginning.

Figure 3:
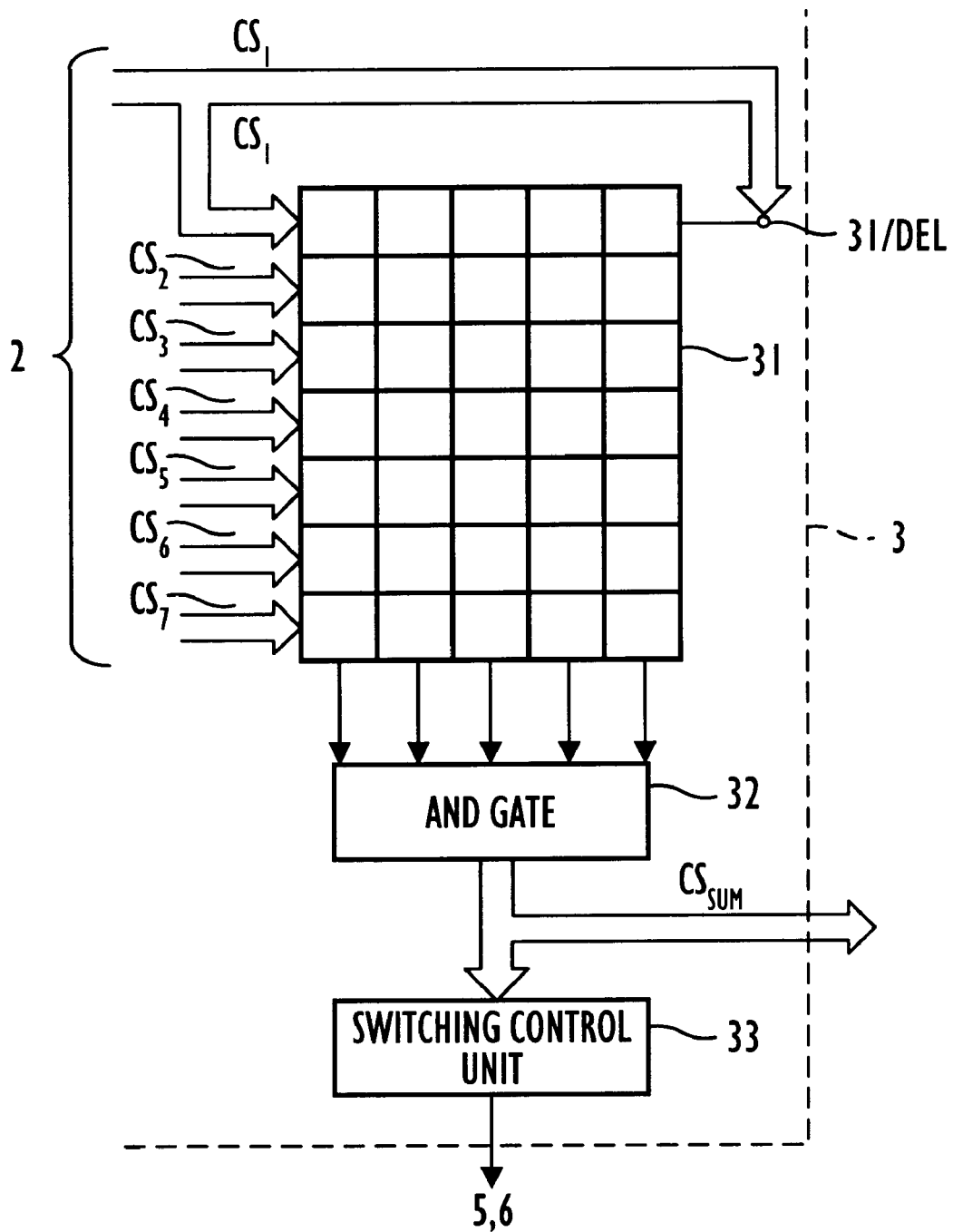
FIG. 3, a function block diagram of an embodiment of the sequence controller 3 of FIG. 1.

The sequence controller 3 of FIG. 1 is therefore preferably embodied—as shown in FIG. 3—such that a partial outcome memory 31 is provided, which has seven lines and x columns, in which a predetermined number x of successive test passes can be stored in memory, and the associated last x sets of classification signals $cs_1$ through $cs_7$ of FIG. 1a (and/or—which is not shown in FIG. 3—the evaluation outcome "VT condition" derived from them as in FIGS. 2a–2c) are stored in memory. Connected to the output of the memory 31, which is organized on the FIFO principle, is a logical linking unit (a multi-stage AND gate) 32, which after each new pass links the outcomes of the last x passes with a total statement signal $cs_{sum}$, which is delivered to a switching control unit 33 for the therapeutic devices 5, 6. The signal $cs_1$ finally reaches a delete input of the memory 31, which is thereby deleted if $cs_1$ in the current pass has a value that represents the aforementioned range (1).

The total outcome $cs_{sum}$, at least, can also be displayed on the display unit 7, but the classification signals and/or evaluations for each test pass can also be displayed individually, so that from the display the physician can make a subjective overall evaluation, and in case of doubt he can continue the test for longer, or repeat it.

The definitive statement about the presence of ventricular fibrillation is preferably made if in y measurements within a total number of z measured ventricular intervals—y and being programmable—the ventricular fibrillation condition ("VF condition") can be found.

Figure 4:
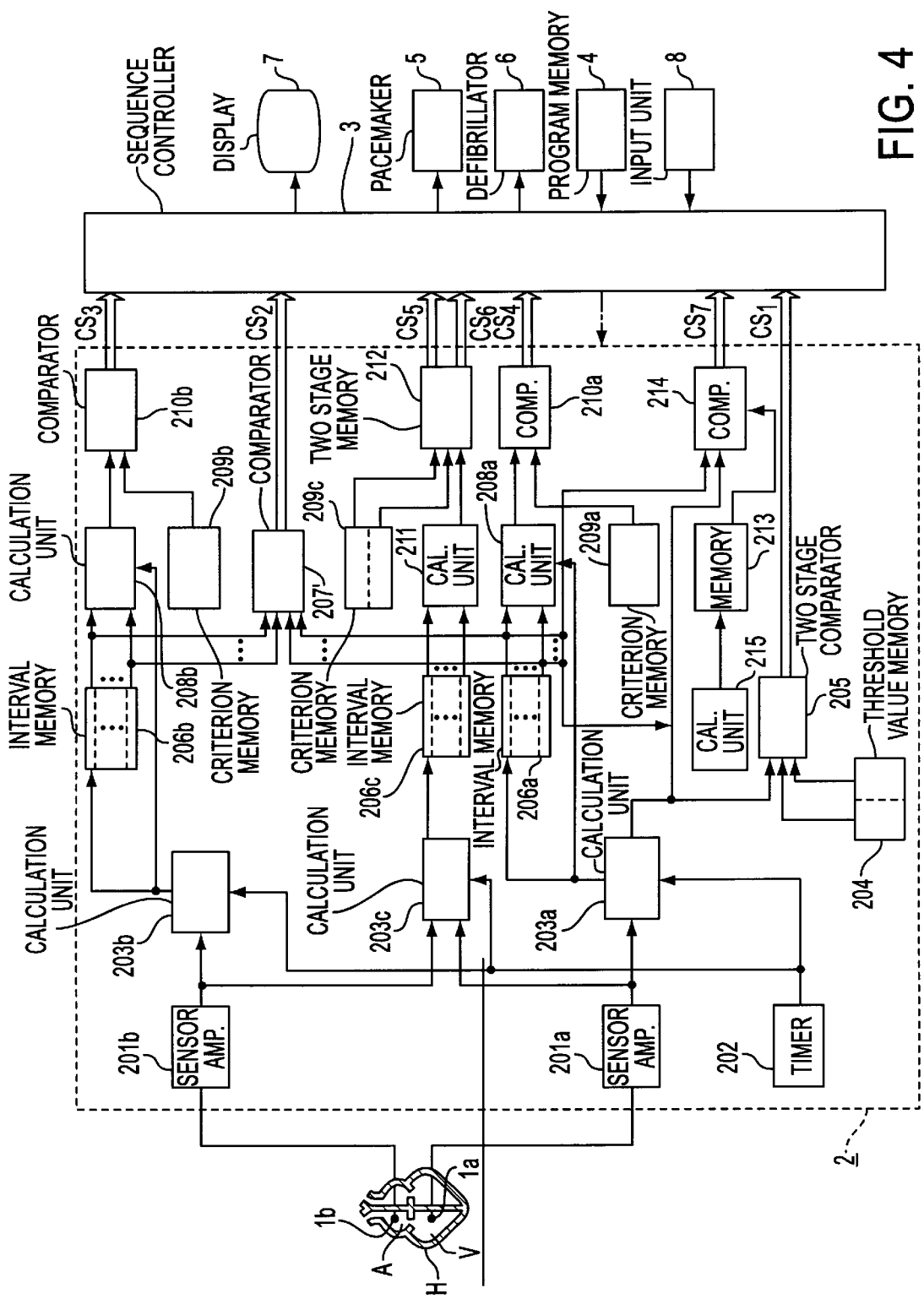
FIG. 4, a function block diagram of an apparatus according to a further embodiment of the invention.

FIG. 4 shows another embodiment of the apparatus according to the invention which is the same as the embodiment illustrated in FIG. 1 with the exception that the inputs of a further comparator 207' are received from the interval memories 206a and 206b, whereas in FIG. 1 the inputs of further comparator 207 are received from the first and second calculation units 203a and 203b, respectively. Corresponding, FIG. 4a, which is a detailed function block diagram of comparator 207', is identical to FIG. 1a with the exception that the inputs to divider 207.1 are received from interval memories 206a and 206b, respectively, instead of from the first and second calculation units 203a and 203b as in FIG. 1a.

Figure 4A:
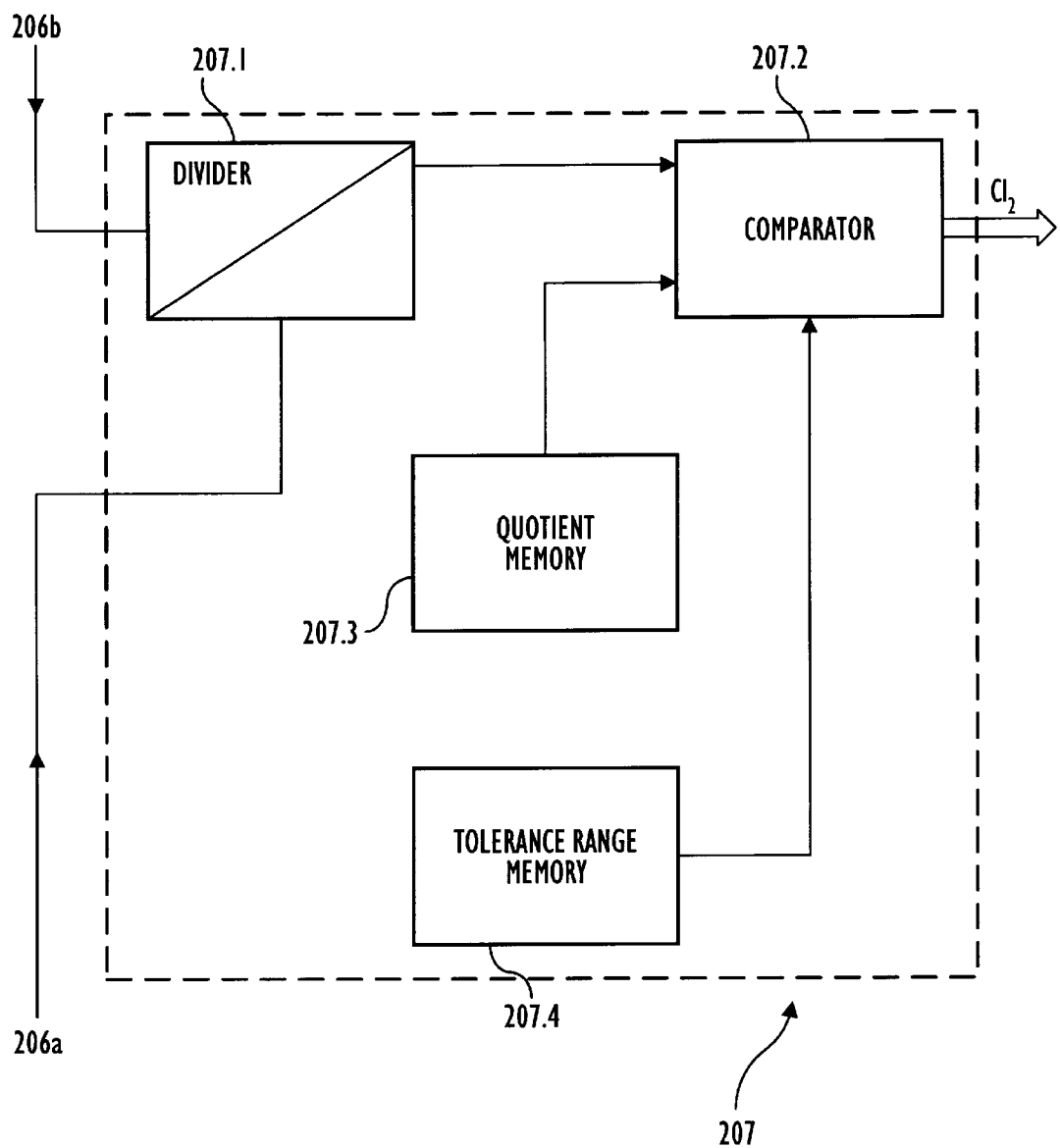
FIG. 4a, a detailed function block diagram of the internal layout a function unit of the apparatus according to FIG. 4.

The apparatus according to FIGS. 4 and 4a operates in the same manner as the apparatus according to FIGS. 1 and 1a and like references numerals are used to identify like elements.

FIG. 5 shows yet another embodiment of the invention wherein, again, elements which are the same as in FIG. 1 are designated by like reference numerals. The only difference between the embodiments of FIGS. 1 and 5 is that in FIG. 5, third and fourth calculation units 208a' and 208b' receive their inputs from the first and second calculation units 203a and 203b, respectively, whereas in FIG. 1, the third and fourth calculation units 208a and 208b receive their input from the interval memories 206a and 206b. Otherwise, the description relating to FIG. 1 equally applies to the description of FIG. 5.

The invention, in terms of how it is embodied, is not limited to the preferred exemplary embodiment described above. On the contrary, a number of variants which make use of the provisions shown, even in a different kind of embodiment, are conceivable.

I claim:

1. An apparatus for detecting ventricular tachycardia, comprising an atrium sensor for sensing electrical activity in an atrium and a ventricle sensor for sensing electrical activity in a ventricle of a heart;

a timer for detecting an instant of occurrence of the respective electrical activity;

a first and second calculation unit, each having an input side connected to the ventricle sensor and the atrium sensor, respectively, and to the timer, for calculating R—R or P—P intervals between successive electrical activities in the ventricle and in the atrium, respectively, and for selectively forming mean R—R and mean P—P interval values over a predetermined period of time or a predetermined number of calculated R—R and P—P intervals, respectively;

a threshold memory for storing at least one threshold value for the R—R intervals or mean R—R interval values;

a first comparator unit, connected to the outputs of the first calculation unit and of the threshold value memory, for comparing the R—R intervals or mean R—R interval values with the at least one threshold value and for outputting a first classification signal characterizing the outcome of the comparison;

first and second interval memory units, connected to the output of the first and second calculation units, respectively, for storing a predetermined number of respective calculated R—R or P—P intervals, or mean R—R or mean P—P interval values in memory;

second comparator unit, connected to the output of one of (a) the first and second calculation units and (b) the first and second interval memory units, for comparing the P—P intervals with the R—R intervals and for outputting a second classification signal characterizing the outcome of the comparison;

a third and fourth calculation unit, connected to the output of at least one of (a) the first and second calculation units and (b) the first and second interval memory units, respectively, for calculating a change over time between successive R—R and P—P intervals or the mean R—R and mean P—P interval values, first and second criterion memories for storing, respectively, a predetermined stability criterion for the change over time between successive R—R and P—P intervals or mean R—R and mean P—P interval values; and a third and fourth comparator unit, each having an input side connected to the output of the third and fourth calculation units, respectively, and to the first and second criterion memories, respectively, for comparing the calculated change over time in the R—R or P—P intervals with an associated stability criterion stored in the respective criterion memory and for outputting a third and fourth classification signal characterizing the outcome of the comparison.

2. The apparatus of claim 1, wherein the second comparator unit includes a divider, a quotient memory, a tolerance range memory and a comparator stage, and the divider has inputs connected to the outputs of one of (a) the first and second calculation units and (b) the first and second interval memory units; the output of the divider is connected to an input of the comparator stage; and the comparator has further inputs connected to the output of the quotient memory and of the tolerance range memory, respectively, such that the divider calculates a quotient from the R—R and P—P intervals or mean R—R and mean P—P interval values stored in memory, and the calculated quotient is tested in the comparator stage for whether it represents an integer within a predetermined tolerance range.

3. The apparatus of claim 1, further comprising:

a fifth calculation unit having an input side connected to the atrium sensor, the ventricle sensor and the timer, for calculating a P-R interval between a respective electrical activity in the atrium and a chronologically next activity in the ventricle, and for selectively forming a mean P-R interval value over a predetermined period of time or a predetermined number of calculated time intervals;

a third interval memory, connected to the output of the fifth calculation unit, for storing a predetermined number of calculated P-R intervals or mean P-R interval values, respectively;

a sixth calculation unit, connected to the output of at least one of the fifth calculation unit and the third interval memory, for calculating changes over time between successive P-R intervals or mean P-R interval values;

a third criterion memory for storing a predetermined regularity and a monotony criterion for the change over time in the P-R intervals or mean P-R interval values; and a fifth comparator unit having an input side connected to the output of the sixth calculation unit and to the third criterion memory, for comparing the calculated change over time in the P-R intervals with the regularity and monotony criterion stored in memory and for outputting a fifth and sixth classification signal characterizing the outcome of the comparison.

4. The apparatus of claim 3, wherein at least one of the first, second and fifth calculation units includes: an interval number memory for storing a predetermined number of intervals to be detected for time averaging; an addition and integration stage, connected to the output of the interval number memory, for determining a total duration of the stored number of successive intervals; and a division stage, connected to the output of the addition and integration stage and of the interval number memory, for forming the respective mean interval value.

5. The apparatus of claim 3, wherein the first, second and third interval memories each have at least three separate memory regions.

6. The apparatus of claim 3, wherein at least one of the third, fourth and sixth calculation units is for performing a calculation of a trend in development over time among more than two of the time intervals calculated in a respective one of first, second and fifth calculation units or stored in a respective one of the first, second and third intervale memory units.

7. The apparatus of claim 1, further comprising: a comparison value memory for storing an R—R comparison interval or an R—R deviation amount and a further comparator unit having an input side connected to the outputs of the first calculation unit, the first interval memory and the comparison value memory, for comparing a current R—R interval or mean R—R interval value with the R—R comparison interval stored in memory or a preceding R—R interval, taking into account the R—R deviation amount and for outputting a further classification signal characterizing the outcome of the comparison.

8. The apparatus of claim 7, further comprising a comparison value calculation unit, having an input connected to the output of the first interval memory for calculating on an ongoing basis the R—R comparison interval or the R—R deviation amount from the current R—R interval and wherein the comparison value memory has an input side connected to an output of the comparison value calculation unit.

9. The apparatus of claim 1, further comprising a flow control device and a program memory for controlling the operation of the apparatus in accordance with a flowchart stored in memory by sequential polling and processing of the classification signals into control signals for controlling at least one of individual components of the apparatus and automatic activation of a cardiac therapy device associated with the apparatus.

10. The apparatus of claim 9, wherein the flow control device includes:

a partial outcome memory having a plurality of columns and a delete input, wherein the classification signals, obtained in one of a predetermined number of successive test passes and/or condition statements are each delivered to one column, and the entire contents of the partial outcome memory are deleted automatically in the presence of the first classification signal having a certain value; and a logical processing unit having inputs connected separately with the outputs of the individual columns, wherein the memory contents of the partial outcome memory are linked in columns, in each case after a test pass, and from this a total calculation signal is obtained with regard to the presence of a ventricular tachycardia (VT condition).

* * * * *